(12) United States Patent
Kendall et al.

(10) Patent No.: US 11,440,081 B2
(45) Date of Patent: Sep. 13, 2022

(54) OPTICAL CORED WIRE IMMERSION NOZZLE

(71) Applicant: HERAEUS ELECTRO-NITE INTERNATIONAL N.V., Houthalen (BE)

(72) Inventors: Martin Kendall, Zonhoven (BE); Marc Straetemans, Hechtel-Eksel (BE); Dominique Feytongs, Hasselt (BE)

(73) Assignee: HERAEUS ELECTRO-NITE INTERNATIONAL N.V., Houthalen (BE)

( * ) Notice: Subject to any disclaimer, the term of this patent is extended or adjusted under 35 U.S.C. 154(b) by 79 days.

(21) Appl. No.: 16/314,550

(22) PCT Filed: Aug. 24, 2017

(86) PCT No.: PCT/EP2017/071365
§ 371 (c)(1),
(2) Date: Dec. 31, 2018

(87) PCT Pub. No.: WO2018/041721
PCT Pub. Date: Mar. 8, 2018

(65) Prior Publication Data
US 2019/0201968 A1   Jul. 4, 2019

(30) Foreign Application Priority Data
Sep. 1, 2016   (EP) ..................................... 16186834

(51) Int. Cl.
*G01K 1/02*       (2021.01)
*B21F 1/02*       (2006.01)
(Continued)

(52) U.S. Cl.
CPC .............. *B21F 1/02* (2013.01); *C21C 7/0056* (2013.01); *C22B 9/05* (2013.01); *F27D 3/0026* (2013.01);
(Continued)

(58) Field of Classification Search
CPC .......... G01J 5/004; G01J 5/0821; G01J 5/048; G01J 5/08; G01J 5/042; G01J 5/0205;
(Continued)

(56) References Cited

U.S. PATENT DOCUMENTS 2,443,028 A * 6/1948 Edwards .................. B66C 13/23
                                                        254/362
3,619,317 A * 11/1971 Shulver ................. B29B 15/125
                                                        156/196
(Continued)

FOREIGN PATENT DOCUMENTS

DE        19623194 C1    7/1997
DE        19916235 A1    9/2000
(Continued)

OTHER PUBLICATIONS

International Search Report issued in PCT/EP2017/071365 dated Oct. 10, 2017.

*Primary Examiner* — Gail Kaplan Verbitsky
(74) *Attorney, Agent, or Firm* — Blank Rome LLP

(57) ABSTRACT

The invention concerns a method for feeding an optical cored wire into a molten metal bath and an immersion system and an immersion nozzle to carry out the method. The optical cored wire (6) is decoiled, a feeding and straightening device (4) with a plurality of rollers (20, 21) conducts feeding of the optical cored wire (6) in a feeding direction towards the metal bath (11) as well as a first straightening of the optical cored wire (6), and subsequently a separated further plurality of non-motor driven nozzle (Continued)

Figure 1A:
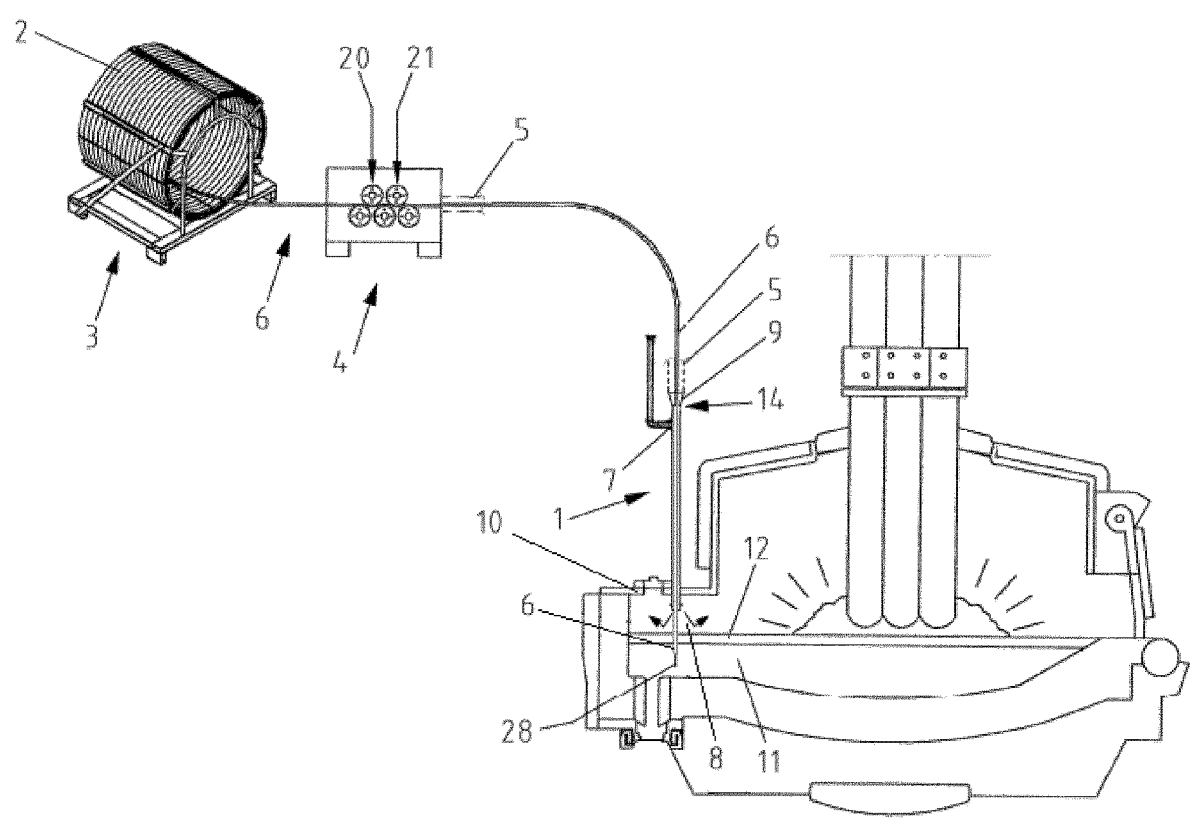

straighteners (13) arranged between the feeding and straightening device (4) and the metal bath (11) conducts a second straightening of the optical cored wire (6). Very high precision of temperature measurement can thereby be achieved.

20 Claims, 6 Drawing Sheets

(51) Int. Cl.
| | |
|---|---|
| *G01J 5/00* | (2022.01) |
| *G01J 5/0821* | (2022.01) |
| *G01J 5/02* | (2022.01) |
| *C21C 7/00* | (2006.01) |
| *F27D 3/00* | (2006.01) |
| *C22B 9/05* | (2006.01) |
| *G01N 33/205* | (2019.01) |
| *F27D 21/00* | (2006.01) |

(52) U.S. Cl.
CPC ............. *G01J 5/004* (2013.01); *G01J 5/0205* (2013.01); *G01J 5/0821* (2013.01); *G01N 33/205* (2019.01); *F27D 21/0014* (2013.01); *F27M 2001/1582* (2013.01); *G01K 1/02* (2013.01)

(58) Field of Classification Search
CPC .. G01J 5/04; G01K 13/00; G01K 1/08; G01K 1/14; G01K 1/16; G01K 1/146; G01K 7/025; G01K 1/00; G01K 17/00; G01K 1/02; G01N 33/205; G01N 1/1409; G01N 25/4806; B22D 27/08; B22D 2/00; B22D 35/00; B21F 1/02; C21C 7/0056; C22B 9/05; F27D 3/0025; F27D 21/0014; F27M 2001/1582
USPC ................... 374/139, 130, 131, 208; 136/234
See application file for complete search history.

(56) References Cited

U.S. PATENT DOCUMENTS

| | | | | |
|---|---|---|---|---|
| 3,692,091 A | * | 9/1972 | Saxer | B22D 9/003 164/337 |
| 4,595,300 A | * | 6/1986 | Kaufman | G01K 1/146 374/170 |
| 4,685,812 A | * | 8/1987 | Sierpinski | C10B 41/00 374/132 |
| 5,283,852 A | * | 2/1994 | Gibler | G02B 6/4486 385/102 |
| 5,585,914 A | | 12/1996 | Yamasaki et al. | |
| 5,730,527 A | * | 3/1998 | Takayama | G01J 5/041 374/127 |
| 6,227,702 B1 | * | 5/2001 | Yamada | G01K 1/125 266/88 |
| 8,282,704 B2 | | 10/2012 | Poulalion | |
| 9,863,709 B2 | * | 1/2018 | Neyens | F27D 11/08 |
| 9,919,373 B2 | * | 3/2018 | Lopez | B65H 49/205 |
| 10,024,732 B2 | * | 7/2018 | Neyens | G01J 5/04 |
| 10,078,194 B2 | * | 9/2018 | Sajima | G02B 6/448 |
| 10,514,302 B2 | * | 12/2019 | Kendall | G01K 1/026 |
| 2002/0025434 A1 | | 2/2002 | Riche et al. | |
| 2003/0002560 A1 | * | 1/2003 | Yamanaka | G01J 5/004 374/139 |
| 2003/0074944 A1 | * | 4/2003 | Stjepan | B21F 23/002 72/140 |
| 2006/0114967 A1 | * | 6/2006 | Dams | G01J 5/0044 374/E13.013 |
| 2007/0268477 A1 | | 11/2007 | Dams et al. | |
| 2008/0236778 A1 | * | 10/2008 | Colavito | C21C 7/0075 164/47 |
| 2009/0074028 A1 | | 3/2009 | Lamp et al. | |
| 2010/0007067 A1 | * | 1/2010 | Vermeulen | C21C 7/0056 266/216 |
| 2010/0020845 A1 | * | 1/2010 | Dams | G01J 5/061 374/139 |
| 2011/0280278 A1 | * | 11/2011 | Cuypers | G01J 5/004 374/139 |
| 2014/0321504 A1 | * | 10/2014 | Neyens | G01J 5/042 374/139 |
| 2015/0323258 A1 | | 11/2015 | Neyens et al. | |
| 2016/0216162 A1 | * | 7/2016 | Neyens | G01J 5/041 |
| 2016/0250687 A1 | * | 9/2016 | Dick | F27D 3/14 239/589 |

FOREIGN PATENT DOCUMENTS

| | | | | |
|---|---|---|---|---|
| EP | 0596134 A1 | | 5/1994 | |
| EP | 0802401 A1 | | 10/1997 | |
| FR | 2906538 A1 | | 4/2008 | |
| JP | 03186724 A | * | 8/1991 | |
| JP | 09079909 A | * | 3/1997 | |
| JP | H0979909 A | | 3/1997 | |
| JP | H09159534 A | | 6/1997 | |
| JP | H10160578 A | | 6/1998 | |
| JP | 10185698 A | * | 7/1998 | |
| JP | H10270950 A | | 10/1998 | |
| JP | H11132858 A | | 5/1999 | |
| JP | H11142246 A | | 5/1999 | |
| JP | 2003021560 A | | 1/2003 | |
| KR | 10170174 B1 | * | 9/2017 | |
| RU | 2721019 C1 | * | 5/2020 | ............... B21F 1/02 |
| WO | WO-9716709 A1 | * | 5/1997 | ............. G01J 5/004 |

\* cited by examiner

OPTICAL CORED WIRE IMMERSION NOZZLE

CROSS-REFERENCE TO RELATED APPLICATIONS

This application is a national stage of International Patent Application No. PCT/EP2017/071365, filed Aug. 24, 2017, which claims the benefit of Europe Patent Application No. 16186834.4, filed Sep. 1, 2016, each of which are hereby incorporated by reference in their entirety.

The invention concerns a method for feeding an optical cored wire into a molten metal bath and an immersion system and an immersion nozzle to carry out the method.

The need for temperature measurement in metallurgical vessels during the metal making process has provided numerous means to obtain this information. During the manufacture of molten metal, particularly iron and steel, and more particularly the melting environment of an electric arc furnace, it has been found that an immersed optical fiber can be used to receive and carry thermal radiation from the molten metal to a detector and suitable instrumentation to determine the temperature of the molten metal. The immersed optical fiber is consumed at a significantly fast rate to warrant continuous or intermittently continuous feeding of the fiber to determine an accurate temperature over any interval other than a brief moment in time. Consumable optical fibers suitable for practicing the above prior art are known, for example, from JP H10-270950A, JPH11142246A, JP19950316417, U.S. Pat. Nos. 5,585,914 and 8,038,344.

EP 0 802 401A discloses a feeding drive comprising a motor for feeding an optical wire, correcting rolls which remove twist in the metal jacketed optical fiber and pinch rollers for feeding the optical wire. Once initiated, the motor engages the pinch rolls which push the corrected metal jacketed optical fiber into a guide tube. Here also disclosed is a mechanism for cutting away an unusable devitrified section of the fiber before each use.

US 2007/0268477 A1 discloses an optical device for measuring a parameter of a molten bath, the device comprising an optical fiber, a cover laterally surrounding the optical fiber, wherein the cover surrounds the optical fiber in a plurality of layers, one layer comprising an outer metal tube and an intermediate layer arranged beneath the metal tube, the intermediate layer comprising a powder or a fibrous or granular material, wherein the material of the intermediate layer surrounds the fiber in a plurality of pieces.

However, despite the large volume of state of the art of immersion systems and optical cored wire temperature measurement, errors still occur in temperature measurement and there is still a need to improve the measurement precision.

Multi-layered wire structures with a steel outer covering are also used in steelworks to introduce doping substances selectively into the molten steel bath as disclosed in U.S. Pat. No. 8,282,704 A1, DE19916235, DE3712619, DE19623194, U.S. Pat. No. 6,770,366 as well as EP0806640, JP3267122, JPS6052507 and DE 37 07 322. However, despite the large volume of prior art also in this field, U.S. Pat. No. 7,906,747 teaches that error modes still exists also for metallurgical cored wired.

The content of the cited documents are incorporated by reference herein.

The purpose of the invention is to provide a further developed method and apparatus for measuring the temperature of a molten metal bath with an optical cored wire.

For the solution of the problem serves a method for feeding an optical cored wire into a molten metal bath and an immersion system and an immersion nozzle to carry out the method according to the main claim. Preferred embodiments are described in the dependent claims.

The above described features known from the prior art can be combined alone or in combination with one of the below disclosed aspects and embodiments of the invention.

The problem is solved by means of a method for feeding an optical cored wire into a molten metal bath, wherein the optical cored wire is decoiled, a feeding and straightening device with a plurality of rollers conducts feeding of the optical cored wire in a feeding direction towards the metal bath as well as a first straightening of the optical cored wire, and subsequently a separated further plurality of non-motor driven nozzle straighteners, preferably nozzle rollers, arranged between the feeding and straightening device and the metal bath conducts a second straightening of the optical cored wire.

Decoiling means taking the optical cored wire from a wound or curved storing condition for use, for example from a coil or a spool.

Molten metal bath means molten metal, particularly iron and steel, in a vessel and more particularly the melting environment of an electric arc furnace.

Separated further plurality of nozzle straighteners, preferably nozzle rollers, means separated in that separated plurality of nozzle straighteners, preferably nozzle rollers, are not arranged within a same or single housing or mounted on a same or single base element.

Separated plurality of nozzle straighteners, preferably nozzle rollers, are not arranged immediately adjacent to the feeding and straightening device and/or its plurality of rollers, but typically separated therefrom by at least a guide tube, particularly connected to the immersion nozzle by a connector. Particularly, there is only one connector of the immersion nozzle comprised by a system of the feeding and straightening device, the immersion nozzle and connecting means therebetween.

Between the feeding and straightening device and the metal bath means after the feeding and straightening device in feeding direction and above the metal bath surface. The feeding towards or feeding direction towards is typically oriented to immerse the optical cored wire into the molten metal bath.

Another aspect of the invention concerns an immersion nozzle to carry out the above described method for feeding an optical cored wire into a molten metal bath in an immersion direction towards the metal bath, the immersion nozzle comprising a nozzle housing, a plurality of non-motor driven nozzle straighteners, preferably nozzle rollers, inside of the housing and a carrier pipe—particularly at least partly—surrounded by the housing for guiding the optical cored wire, wherein a purge gas inlet allows supply of a purge gas into an annulus outside of the carrier pipe and inside of the housing, wherein a separation separates the plurality of non-motor driven nozzle straighteners from the annulus.

An immersion end of the immersion nozzle in feeding direction and/or the nozzle housing are preferably composed to withstand conditions inside of a vessel containing the molten metal bath. The immersion nozzle in feeding direction and/or the nozzle housing are preferably composed of steel and/or a ceramic material.

A nozzle straighteners refers to means to straighten the optical cored wire. Preferably, the nozzle straightener is a nozzle roller, i.e. a roller within the immersion nozzle.

Alternatively, the nozzle straighteners can also be an aligning device that keeps in direct contact with the optical cored wire from at least two opposed sides, preferably configured to apply pressure on the optical cored wire. Preferably, such aligning device is shaped longitudinally in parallel to the immersion direction.

Non-motor driven nozzle straighteners, preferably nozzle rollers, can only straighten and/or rotate due to interactions, particularly friction forces, with the optical cored wire. Particularly, the immersion nozzle does not comprise a motor or drive to drive a nozzle straightener or roller of the plurality of nozzle straighteners of the immersion nozzle.

Composed to withstand conditions inside of a vessel containing the molten metal bath means resistant to temperatures of for example molten steel.

In particular, the plurality of nozzle straighteners and/or every nozzle straightener of the immersion nozzle is arranged such that a reduction of their operation temperature within the vessel is achieved by the purge gas.

Reliable functionality is thereby achieved.

Preferably, the plurality of nozzle straighteners and/or every nozzle straightener of the immersion nozzle is arranged within a distance to the purge gas inlet which is less than the length of the annulus in immersion direction and/or at most two times (2.0 times) or one and a half times (1.5 times) of the distance between the first and last nozzle straightener measured in immersion direction. The distance is commonly measured between center points of the nozzle straighteners, which are the axis in case of rollers as nozzle straighteners.

Very precise measurement while having the nozzle straighteners being cooled by the purge gas can be achieved.

In particular, the separation immediately separates the plurality of nozzle straighteners and a flow channel for the purge gas. Preferably, the purge gas inlet, the plurality of nozzle straighteners and the annulus form a T-shape.

A compact design of the immersion nozzle can thereby be achieved.

Another aspect of the invention concerns an immersion nozzle to carry out the above described method for feeding an optical cored wire into a molten metal bath in an immersion direction towards the metal bath, the immersion nozzle comprising a plurality of non-motor driven nozzle straighteners, preferably nozzle rollers, and a carrier pipe for guiding the optical cored wire, wherein preferably an immersion end of the immersion nozzle in feeding direction is composed to withstand conditions inside of a vessel containing the molten metal bath.

Another aspect of the invention concerns an immersion system to carry out the above described method for feeding an optical cored wire into a molten metal bath comprising a feeding and straightening device and one of the above described immersion nozzle, wherein the feeding and straightening device comprises a plurality of rollers for feeding the optical cored wire in a feeding direction towards the metal bath as well as a first straightening of the optical cored wire.

The definitions as well as preferred features and embodiments of one of the aspects of the invention also apply to the other aspects of the invention, because they all basically concern the same or substantially same system.

All aspects of the invention disclosed within application are based on the same insight described as following:

A feeding and straightening device known in the state of the art feed and straighten an optical cored wire supplied from a coil or spool in order to enable immersion of the optical cored wire to a certain depths in the melting bath. Bending of the optical cored wire after exiting a simple prior art nozzle was observed. The reasons were assumed to be buoyancy forces of the liquid metal, floating of the optical cored wire towards the surface of the metal bath and fluid currents of the molten bath acting against the optical cored wire with the result of bending in the metal bath.

Since the bending direction usually leaded to an orientation of the tip of the optical cored wire towards the center of the melting bath and away from the vessel wall, said bending was supposed to even improve the quality of temperature measurement and thus be appreciated.

The present invention however is firstly based on the insight that the precision of temperature measurement is rather dependent from a low immersion depth deviation $\Delta z$ of the tip of the optical cored wire at a prescribed immersion depth, i.e. in gravitation direction. In other words, a small deviation in the immersion depth contributes more to a very precise temperature measurement compared to a tip of an optical cored wire bent in a way to be closer oriented towards the center of the metal bath while at the same time having a higher immersion depth deviation.

Secondly, it was found that said bending of the optical cored wire in the metal bath is not only caused by buoyancy forces of the liquid metal and fluid currents of the molten bath, but also caused by the residual cast of the optical cored wire from coiling or spooling.

Figure 7:
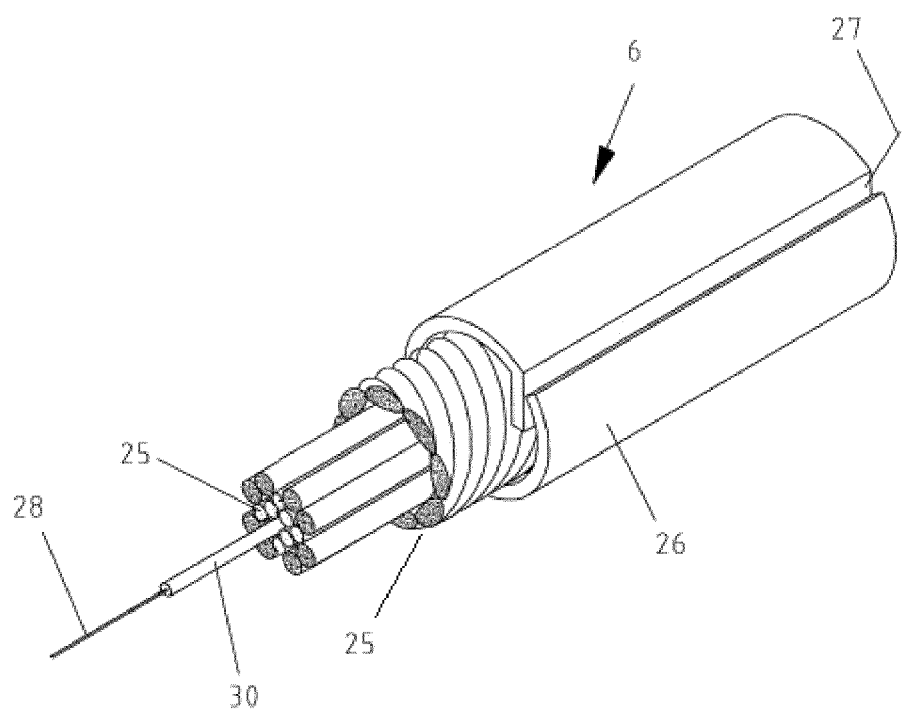

This cast leads on the one hand to inhomogeneous metal structure or texture of the metal jacket of the optical cored wire such that temperature changes and other environmental changes that can occur between the feeding and straightening device and the metal bath lead to additional bending. These changes result from e.g. the different conditions outside and inside the vessel of the furnace and the local cooling of the optical cored wire by means of a purge gas. On the other hand, having an optical cored wire with double layer of metal as shown in FIG. 7, such optical cored wire does not exhibit uniform bending and unbending forces due to the presence of the double layer of metal as well as the seam encompassing a partial arc about the circumference of the wire. This seam resists both the compressive force on the inside of a bend and the tensile force when falling on the outer curve of a bend of the same radius. Because of this, any bending moment will create a twist in the optical cored wire favoring the single wall for deformation. During feeding, as the drive rolls push the optical cored wire through a guide tube, the single walls becoming aligned with a curve in the guide tube may also cause a cast in the cored wire preventing it from returning to its original straightened condition when outside the confinement of the guide tube causing the optical cored wire to deviate from the immersion direction. The cored wire typically has an inner metal layer formed by metal under the seam as well as an outer metal layer which is the metal over the seam. During the feeding process, the cored wire will be typically pulled through a series of straightening rolls or rollers of the feeding and straightening device, which reduces the cast—obtained at the time of loading onto the spool or coil—of the outer layer of metal to a higher extent than that of the inner layer of metal. Therefore, during feeding and immersion the optical cored wire into the melting bath and leaving any guiding tube or pipe, this higher remained cast of the inner metal layer will contribute to the bending and to deviate from the immersion direction.

Figure 1B:
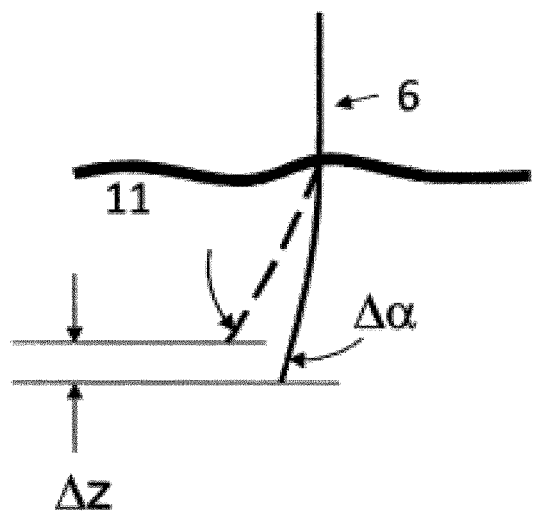
Figure 1C:
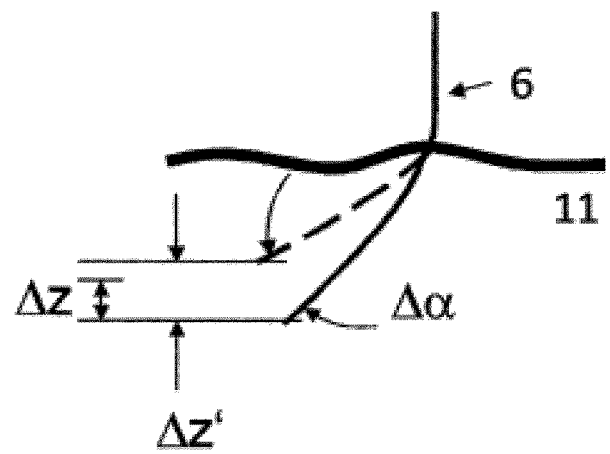

Thirdly, combining the above first and second findings with the insight that reduced bending leads to reduced immersion depth deviation $\Delta z$ of the tip of the optical cored wire as illustrated in the FIGS. 1b and 1c, resulted in the invention to provide straightening inside of the immersion nozzle or a second straightening between the feeding and straightening device and the metal bath.

Thereby, the portion of bending in the metal bath caused by said effects on the way from the feeding and straightening device to the metal bath can be reduced. This enables a very small immersion depth deviation and thus very high temperature measurement precision.

A feeding and straightening device with a plurality of rollers according to the above described aspects of the invention, i.e. method for feeding an optical cored wire into a molten metal bath and/or an immersion system to carry out the method, covers at least the following embodiments:

In one embodiment, all rollers of the feeding and straightening device are motor driven. This enables very effective feeding.

In one embodiment, some rollers of the feeding and straightening device are motor driven that feed and straighten the optical cored wire while other rollers of the feeding and straightening device are not motor driven that only straighten the optical cored wire. This enables high straightening effect with low complexity of the device.

In one embodiment, only motor driven rollers of the feeding and straightening device feeds the optical cored wire and only non-motor driven rollers of the feeding and straightening device straighten the optical cored wire. This enables targeted straightening by using rollers tailored to obtain said targeted straightening effects.

In one embodiment, motor driven rollers and non-motor driven rollers of the feeding and straightening device are arranged inside of one single housing, thus not in separated units. This enables a compact device.

In one embodiment, the feeding and straightening device is formed by two separated housings, wherein the two housings are connected by a guide pipe, wherein in the first housing are arranged motor driven rollers for feeding and/or straightening the optical cored wire while in the second housing are arranged non-motor driven rollers for straightening the optical cored wire. This enables adaptation of the feeding and straightening device to the available space.

Preferably, immersing of the optical cored wires is accomplished by two separated housings, wherein the two housings are connected by a guide pipe, wherein in the first housing are arranged motor driven rollers for feeding and/or straightening the optical cored wire while in the second housing are arranged non-motor driven rollers for straightening the optical cored wire just before entering the molten metal. This enables optimum feeding and optimum straightening of the optical cored wire in preparation for immersion.

The features of each embodiment as well as features of the above description and the features of the figure description can be combined with each other and combined with the subject matter of the aspects of the invention and each claim.

Details and further advantages are provided in the following description of the figures which depicts a preferred execution example with the necessary details and individual components.

FIG. 1a: An optical cored wire immersion system with an immersion nozzle

FIG. 1b: Illustration of the immersed optical cored wire position deviation

FIG. 1c: State of the art immersed wire position deviation

Figure 1D:
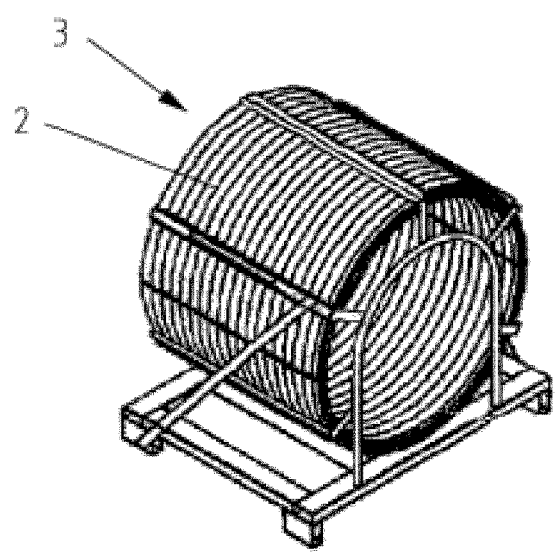

FIG. 1d: An optical cored wire spool

Figure 2:
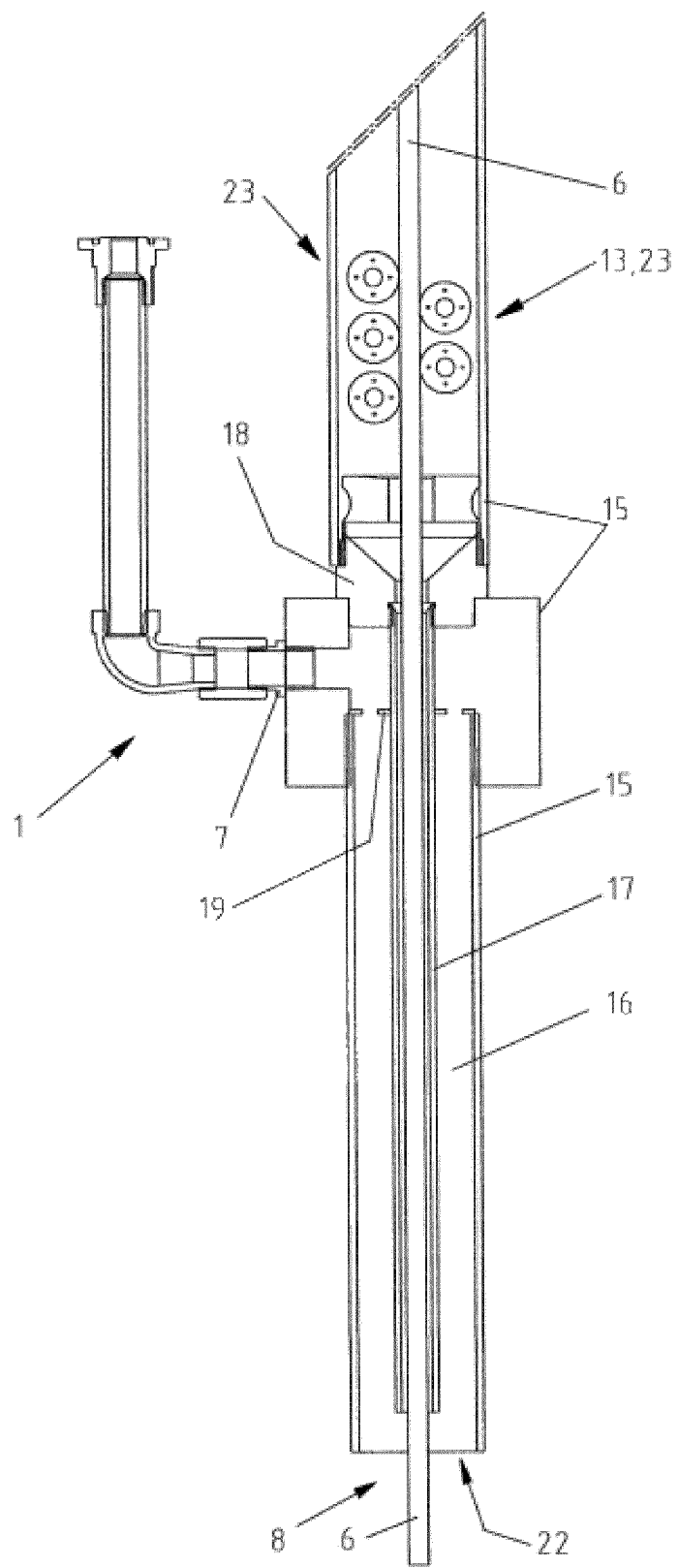

FIG. 2: An immersion nozzle with integrated wire straightener

Figure 3:
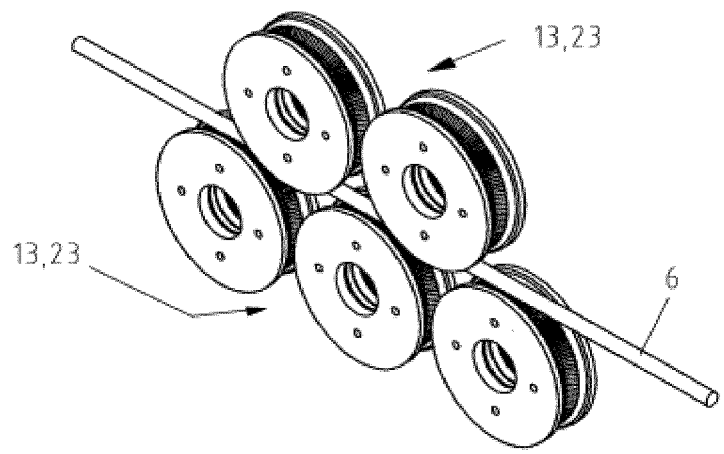

FIG. 3: A wire straightener with opposed rollers

Figure 4:
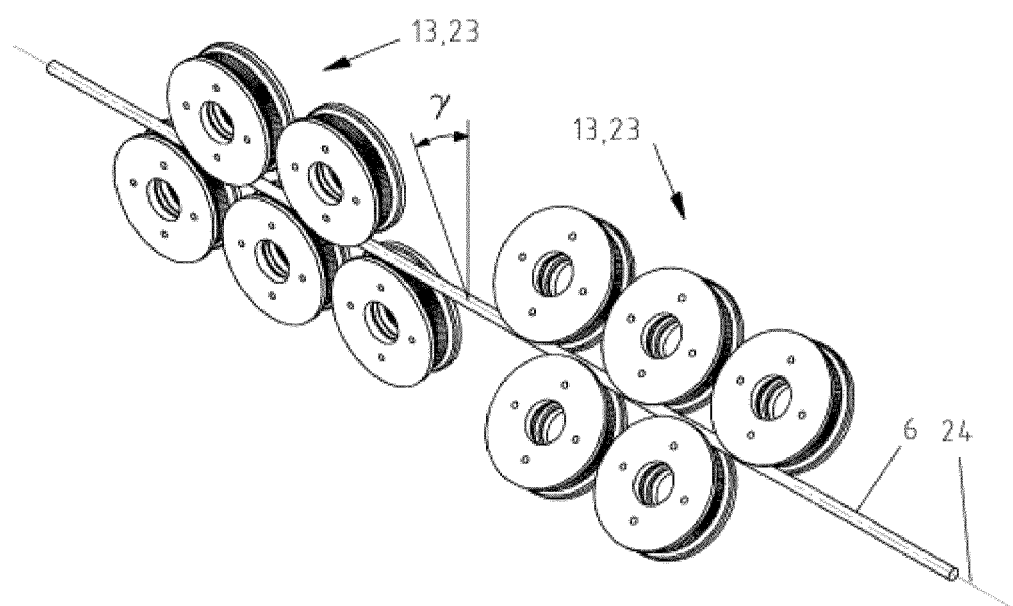

FIG. 4: A wire straightener with rollers at an offset angle

Figure 5:
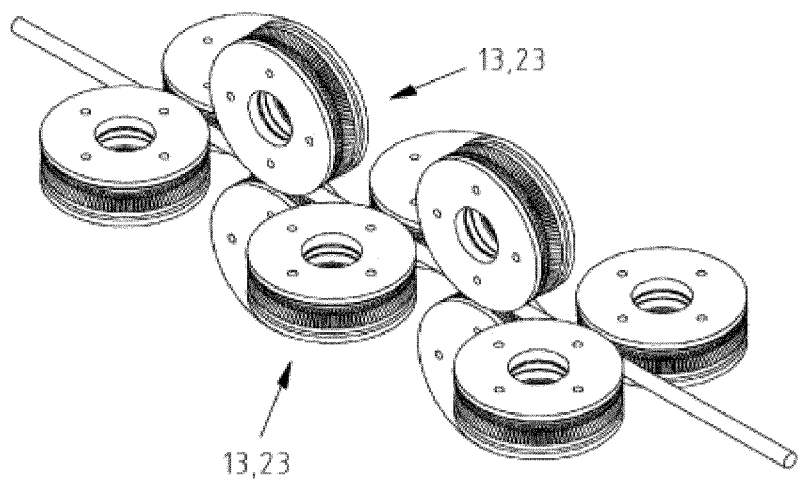
Figures 6A, 6B, 6C, 6D:
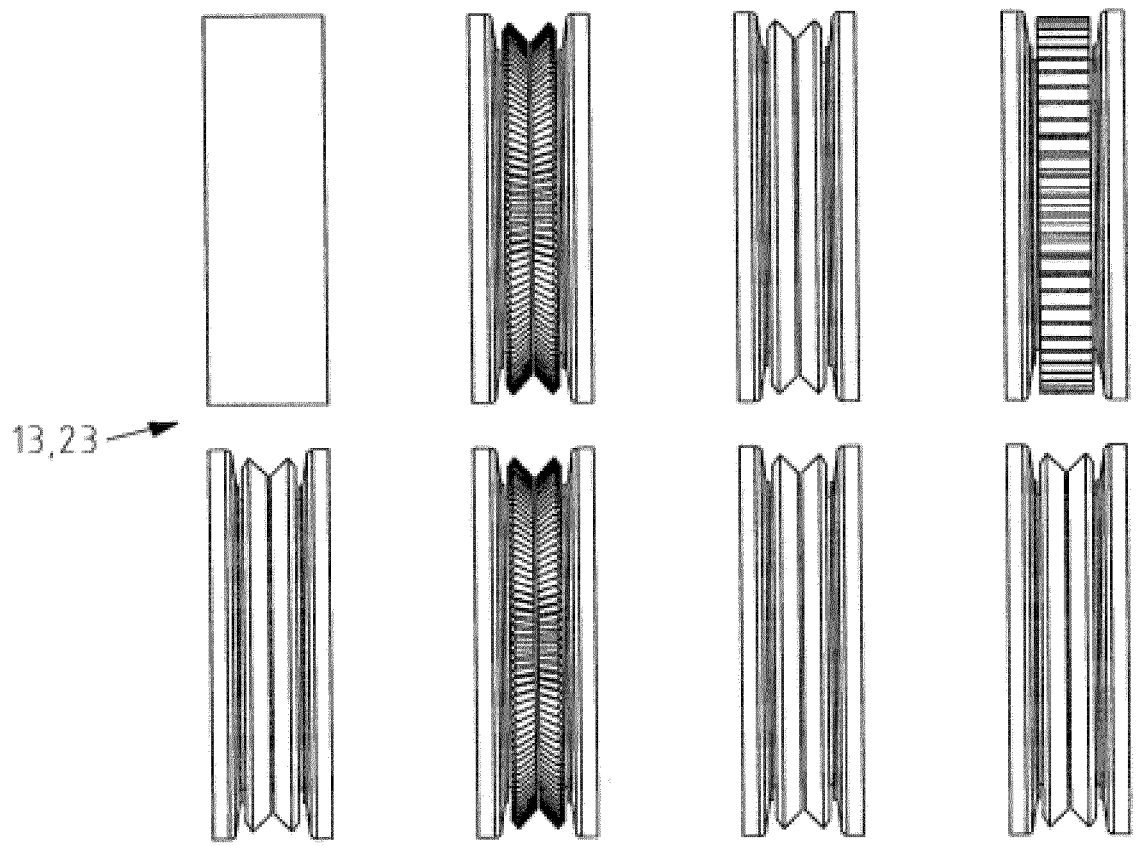

FIG. 5: A wire straightener with internal offset rollers

FIGS. 6a to 6d: Different combinations of surface and shape in a pair of rollers FIG. 7: Partly sectioned view of an optical cored wire FIG. 8: Cross section view of an optical cored wire Based on the immersion system shown in FIG. 1a and the immersion nozzle 1 shown in FIG. 2, the method for feeding an optical cored wire 6 into a molten metal bath 11 can be illustrated. The optical cored wire 6 is first decoiled particularly from a coil 2 and a feeding and straightening device 4 with a plurality of rollers 20, 21 conducts feeding of the optical cored wire 6 in a feeding direction towards the metal bath 11 as well as a first straightening of the optical cored wire 6. Preferably, all rollers 20, 21 or pairs of rollers 20, 21 can be driven by a motor and can feed and straighten the optical cored wire 6. It is possible to just drive the first pair of rollers 20 for feeding and use the other rollers 21 and/or pairs of rollers 21 non-motor driven for straightening the optical cored wire 6. Decoiling can also be conducted from a spool 3 as shown in FIGS. 1a and 1d.

In one embodiment, a pair of rollers 20, 21 of the feeding and straightening device 4 and/or a pair of nozzle straighteners 23 of the plurality of non-motor driven nozzle straighteners 13 of the immersion nozzle 1 can comprise two opposed rollers particularly being arranged on a vertical relative to the feeding direction of the optical cored wire 6.

In one other embodiment, a pair of rollers 20, 21 of the feeding and straightening device 4 and/or a pair of nozzle straighteners 23 of the plurality of non-motor driven nozzle straighteners 13 of the immersion nozzle 1 can comprise two opposed rollers particularly being arranged on a tilted line, i.e. imaged virtual straight line, particularly 30° to 60° tiled, relative to the feeding direction of the optical cored wire 6 as exemplarily shown by the first two rollers 20 or last two rollers 21 in FIG. 1a.

Opposed rollers being arranged particularly refers to the arrangement of the roller pivot axis.

Subsequently, a separated further plurality of non-motor driven nozzle straighteners 13 arranged between the feeding and straightening device 4 and the metal bath 11 conducts a second straightening of the optical cored wire 6. By thereby compensating bending facilitating effects caused on the way between the feeding and straightening device 4 and the immersion nozzle 1, bending of the optical cored wire 6 in the metal bath 11 (FIG. 1c) can be reduced and measurement precision increased.

FIG. 1b illustrates an immersed optical cored wire 6 according to the invention while FIG. 1c shows an immersed optical cored wire 6 according to the state of the art. In this contrasting juxtaposition, a same angular position deviation $\Delta\alpha$ is illustrated, although the angular position deviation shall be reduced when applying the invention. Nevertheless, even at same angular position deviation $\Delta\alpha$, is becomes evident, that the immersion depth deviation $\Delta z$ when applying the invention is smaller than the immersion depth deviation $\Delta z'$ of the state of the art. Higher temperature measurement precision can thereby be achieved when applying the invention.

In one embodiment, an immersion nozzle 1 (FIG. 1a, FIG. 2) between the feeding and straightening device 4 and the metal bath 11 comprises the separated further plurality of non-motor driven nozzle straighteners 13 and releases the optical cored wire 6 typically through a nozzle exit 8 above a surface of the metal bath 11. This enables reduced bending of the optical cored wire 6 exiting the nozzle and into the metal bath 11 and very precise temperature measurement.

Releasing an optical cored wire 6 particularly by an immersion nozzle 1 means that inside of the vessel, the optical cored wire 6 is moving out of an exit of a guiding and/or protecting surrounding without subsequent connected guiding means for example by a guiding tube 5 or carrier pipe 17 such that the optical cored wire 6 is fed freely inside the vessel towards the feeding direction.

In one embodiment, a purge gas is released in feeding direction around or encompassing the released optical cored wire 6. This helps to keep the nozzle exit 8 open for unimpeded passaging and free of contamination, cools the portion of the optical cored wire just inside the immersion nozzle and cools a portion of the optical cored wire just exiting the immersion nozzle.

In one embodiment, the optical cored wire 6 is released in a distance closer to metal bath that a vessel wall 10, preferably in a distance of at least 10 cm, preferably at least 20 cm, and/or at most 100 cm, preferred at most 50 cm, to a metal bath surface. Highly precise measurements can thereby be enabled. In one embodiment, the optical cored wire 6 is immersed into the metal bath 12 under a right angle to a surface of the metal bath 12. Highly precise measurements can thereby be enabled.

FIG. 1a shows a long length of optical cored wire 6 being coiled 2 or supplied on a spool 3 is pulled by the drive rollers 20 of the feeding and straightening device 4, wherein the drive rollers 20 are motor-driven. Particularly, the rollers 21 perform a first straightening of the optical cored wire 6 and can be composed motor-driven or non-motor driven. The drive rollers 20 can preferably also contribute to straightening of the optical cored wire 6.

The feeding and straightening device 4 can be optionally comprising or divided into two parts in feeding direction, wherein the first part comprises rollers 20 for feeding the optical cored wire 6 in feeding direction towards the melting bath and a second part comprises rollers 21 for straightening the optical cored wire 6.

At the exit of the feeding and straightening device 4—i.e. on the opposite of the entrance of the feeding and straightening device 4—, the optical cored wire 6 is pushed into a guide tube 5 for guiding the optical cored wire 6 to the immersion nozzle 1.

The guide tube 5 typically has an inner diameter of at least 1.5 times, preferably 2 times, further preferred 3 times, and/or at most 8 times, preferred at most 6 times, the optical cored wire outer diameter.

The guide tube 5 preferably spans the distance between the exit of the feeding and straightening device and the nozzle entry 14 of the immersion nozzle 1 to avoid collection of dust and dirt within the guide tube 5 which would increase the drag between the optical cored wire 6 and guide tube 5. The guide tube 5 is preferably a sectional steel pipe where individual portions can be separated for cleaning or troubleshooting of the feed channel and maybe gas purged. The guide tube 5 or a section of the guide tube 5 can be straight or curved, particularly the guide tube 5 is L-shaped, preferably with a curvature radius higher than the coil or spool radius, particularly high enough to avoid plastic deformation of the optical cored wire 6. This enables to prevent or counteract further bending induction into the optical cored wire 6.

The immersion nozzle 1 is attached to the guide tube 5 at the immersion end, i.e. in feeding direction, of the guide tube 5, preferably by means of a fitting such as a bayonet connector 9. The immersion nozzle 1 itself is not—and is also not composed to be—immersed into the molten bath 11, but facilitates the passage of the optical cored wire 6 to the metal bath 11.

In one embodiment, the immersion nozzle 1 is composed to facilitate the passage of the optical cored wire 6 through the furnace vessel wall 10 into the vessel interior. In other words, the nozzle entry 14 of the immersion nozzle 1 is arranged outside the vessel, then the nozzle housing 15 of the immersion nozzle 1 is passing through the vessel wall 10 and the immersion end of the immersion nozzle 1 is located inside the vessel. This enables very safe passaging of the optical cored wire through the vessel wall 10. Alternatively, the entire immersion nozzle can be arranged within the vessel.

Particularly, the immersion nozzle 1 has a tube shape that preferably expands in feeding direction. Preferably, the immersion nozzle 1 has only one single nozzle housing 15 for housing all immersion nozzle components such as the plurality of non-motor driven nozzle straighteners 13 and/or a carrier pipe 17 for guiding the optical cored wire 6 to the nozzle exit 8.

Preferably, the nozzle housing 15 comprises one or exactly one housing part for housing all nozzle straighteners 13 of the immersion nozzle 1. In particular, said exactly one housing part comprises or consists of a one piece and/or exactly one tube, a one piece and/or exactly one separation element 18, and/or a one piece and/or exactly one connector 9.

Preferably, the nozzle housing 15 comprises one or exactly one housing part for housing the carrier pipe 17 for guiding the optical cored wire 6 to the nozzle exit 8.

Preferably, an interconnecting housing part is designed to guide the purge gas from a purge gas inlet 7 to the nozzle exit 8 and/or an annulus 16 formed between the carrier pipe 17 and the nozzle housing 15.

In an alternate embodiment, the housing part for housing all nozzle straighteners 13 as the same or substantially same diameter like the housing part for housing the carrier pipe 17. Preferably, the nozzle straighteners 23 implemented as nozzle rollers have a diameter of less than the diameter of the immersion nozzle 1, the nozzle housing 15, the housing part for housing all nozzle straighteners 13 and/or the housing part for housing the carrier pipe 17.

The connector 9, the purge gas inlet 7 and/or the nozzle exit 8 of the carrier pipe 17 may partly stick out of the nozzle housing 15.

Preferably, the carrier pipe 17 remains spaced from the nozzle exit 8 inside the nozzle housing 15 and/or does not sticking out of the nozzle housing 15 or the nozzle exit 8. This helps to reduce clogging and/or destruction of the carrier pipe 17.

Preferably, the nozzle housing 15 has or consists of a tube or pipe shape, especially the housing part for housing all nozzle straighteners 13 with the housing part for housing the carrier pipe 17. The ratio of length to diameter of the immersion nozzle and/or the nozzle housing 15 amounts to at least 3 times, preferably 5 times, and/or at most 50 times, preferably 20 times. This enables to apply sufficient straightening and avoid excessive deformation of the optical cored wire on the way from the plurality of non-motor driven nozzle straighteners 13 to the nozzle exit 8.

In one embodiment, the plurality of non-motor driven nozzle straighteners 13 is arranged in feeding direction prior to the carrier pipe 17 for guiding the optical cored wire 6 to the nozzle exit 8. This enables application of the purge gas in a compact immersion nozzle design.

Preferably, the immersion nozzle 1 has a gas supply inlet 7 which receives a purge gas, which may be selected from air, argon, nitrogen, natural gas and/or carbon dioxide. In one embodiment, the purge gas can exit the immersion nozzle 1 at the purge gas outlet 22 at the distal end of the immersion nozzle housing 15 in the vessel interior.

In general, the end of the nozzle is kept above the molten metal surface and also above the slag surface. Because the slag does not have a constant volume, at times during steel processing it will foam and expand in volume such that at times, the immersion nozzle 1 maybe below the top surface of the slag 12 and thus immersed into the slag 12. In any case, the particularly constant purge of gas insures that the opening of the nozzle exit 14 and purge gas outlet 22 are not blocked by solidified slag 12 and/or chilled droplets of molten metal.

Thus, the immersion nozzle 1 can be designed to provide an entry into the interior of the melting furnace by a gas purged nozzle inserted through the vessel shell or wall 10 and protective bricks such that its exit is above the level of molten metal 11, but can be below that of the top surface of the molten slag 12 during the metal making process.

FIG. 2 shows an example of a dual wall immersion nozzle 1. The immersion nozzle 1 is inserted through the vessel wall 10 of a metallurgical vessel, preferably such that the axis of the carrier pipe 17 corresponds to the feeding direction towards the molten metal 11 to be sampled. Preferably, the opposite end is in communication with the last portion of the guide tube 5. The immersion nozzle 1 can be installed through the vessel wall 10 being a side wall or a roof of the vessel and/or at any angle. The housing part for housing the carrier pipe 17 and/or the carrier pipe 17 can be angulated or curved. This may allow insertion of the immersion nozzle through a side wall of the vessel.

Preferably, the overall length of the immersion nozzle 1 is adjustable. This enables to compensate the distance difference resulting from an angulated installation of the immersion nozzle 1 while keeping a constant or approximately constant distance of the nozzle exit 8 to the top surface of the metal bath 11. High precise temperature measurement can thereby be achieved.

Preferably, the optical cored wire 6 runs through the guide tube 5 into the nozzle entry 14 via a connector 9. Preferably, the connector 9 mechanically locks the guide tube 5 to the immersion nozzle 1, particularly at the nozzle entry 14. Preferably, one portion of the connector 9 is attached to the guide tube 5 with a receiving portion attached to the immersion nozzle 1.

The nozzle entry 14 forms or is at the opposite side of the nozzle exit 8. Preferably, the nozzle entry 14 and the nozzle exit 8 form the boundaries of the nozzle expansion in feeding direction of the optical cored wire 6.

Between the nozzle entry 14 and the nozzle exit 8 of the immersion nozzle 1 are installed a further plurality of nozzle straighteners 23, particularly non-motor driven nozzle straightener 13, preferably nozzle rollers, for straightening the optical cored wire 6 (FIGS. 3 to 5), which are preferably arranged inside of the nozzle housing 15. This further plurality of nozzle straighteners 23, particularly non-motor driven nozzle straighteners 13, forms a second wire straightener.

A purge gas inlet 7 supplies gas to an annulus 16—i.e. ring shaped space—, which is formed between the carrier pipe 17 and the nozzle housing 15, particularly in radial direction, i.e. radial to the feeding direction. Preferably, the purge gas inlet 7 is located outside of the vessel wall 10, i.e. not inside of the vessel walls 10.

Preferably, the nozzle housing 15 is designed to function as a purge pipe of the immersion nozzle 1. The purge gas, which leaves the immersion nozzle 1 at the immersion end through the purge gas outlet 22, pushes away molten slag 12 and splashing metal from the opening ensuring that the optical cored wire 6 exiting the carrier pipe 17 in feeding direction has an unimpeded manner of moving forward.

In one embodiment, a gas tight separation 18 between the plurality of nozzle straighteners 23, particularly non-motor driven nozzle straighteners 13, and the annulus 16 and/or between the plurality of nozzle straighteners 23 and purge gas inlet 7 is provided. This directs the flow of purge gas towards the opening 22. Nevertheless, the plurality of nozzle straighteners 23, particularly non-motor driven nozzle straighteners 13, are still cooled by the separation 18 which is cooled by the purge gas on the other side of the plurality of nozzle straighteners 23. The separation 18 has a pass through hole for the optical cored wire 6 and/or the carrier pipe 17 is directly connected to the separation 18.

Preferably, the separation 18 has a ring shape and/or funnel shape particularly in feeding direction.

In one embodiment, a portion of the purge gas is diverted through a separation 18, particularly being not gas tight, towards the roller assembly for increased cooling.

Exactly one or two, at least one and/or at most three supporting means 19 with openings to facilitate purge gas passaging fixate the carrier pipe for guiding the optical cored wire 6 to the nozzle housing 15. The supporting means 19 preferably have a disk shape with radial notches as openings.

Preferably, one supporting means 19 is arranged flush with the housing part for housing the carrier pipe 17.

In one embodiment, the gas inlet 7 is arranged in the middle between the separation 18 and the supporting means 19, i.e. middle seen in feeding direction. Preferably, there is a T-shaped hollow space for guiding the purge gas, preferably contoured by a line bordered by the separation 18 and the supporting means 19 as well as an orthogonal to that line being bordered by the gas inlet 7.

In one embodiment, an intermediate housing part comprises said hollow space and/or overlaps with the separation 18, the supporting means 19 and/or the gas inlet 7. Overlap means extending into the intermediate housing part for the purpose of connection. Preferably, the intermediate housing part is a connection device, particularly forming part of the nozzle housing 15 or outer surface of the immersion nozzle 1.

In one embodiment, the nozzle housing 15 is particularly gas tight closed around the particularly tube shaped nozzle entry 14 for allowing an optical cored wire 6 to be fed into the nozzle housing 15 respectively the immersion nozzle 1.

In one embodiment, the carrier pipe 17 is at two times and/or at most 20 times, preferably at most 10 times or 5 times, as long as the plurality of non-motor driven nozzle straighteners 13 in feeding direction.

An additional benefit of the purge gas is to keep the immersion nozzle 1 as well as the unused portion of the optical cored wire 1 cool and thus promotes the longevity of the immersion nozzle 1 and at the same time prevents the devitrification of the unused optical fiber of the optical cored wire 1. Light entering the optical fiber and transmitted along a fiber length that has not been devitrified by exposure to heat prior to immersion, enables reduced errors in temperature measurement. Preferably, the gas pressure is maintained between at least 2 bar and/or at most 5 bar which facilitates sufficient cooling to maintain an un-devitrified fiber.

FIG. 3 is a detailed view of the plurality of non-motor driven nozzle straighteners 13 in form of nozzle rollers of FIG. 2 that form a wire straightener. In one embodiment, at least two, three or five and/or at most ten nozzle straighteners 23 form the plurality of non-motor driven nozzle straighteners 13. Thereby, straightening the optical cored wire 6 for very precise temperature measurement can be obtained.

In one embodiment, the plurality of non-motor driven nozzle straighteners 13, in particular nozzle rollers, of the immersion nozzle 1 is arranged such that each nozzle straightener 23 is placed with a distance in feeding direction to its immediate neighboring nozzle straightener 23 and placed at another angle γ about an axis 24 in feeding direction. In FIG. 3, said angle γ is 180 degree, thus opposing nozzle straighteners 23.

In FIG. 4, said angle γ is 180 degree alternating for the first five neighboring nozzle straightener 23 as well as the five following adjacent nozzle straightener 23, wherein an offset angle γ of at last 30 degree and/or at most 60 degree is present between the last nozzle straightener 23 of the first five nozzle straighteners 23 and the first nozzle straightener 23 of the last five nozzle straighteners 23. This enables reducing twisted bending of the optical cored wire.

Although other embodiments in FIGS. 4 and 5 show alternative configuration for the wire straightener, incorporation onto or into the immersion nozzle 1 of a means to de-strain the optical cored wire 6 after having been pushed through the guide tube 5 promotes the accurate penetration direction of the cored wire.

FIG. 5 shows an arrangement of at least two pairs of opposed nozzle straightener 23, in particular nozzle rollers, wherein each pair of nozzle straighteners 23 is arranged under a right angle to the preceding and following neighboring pair of nozzle straighteners 23. This enables reducing multidirectional bending of the optical cored wire.

FIGS. 6a to 6d show different combinations of surface and shape in a pair of nozzle straightener 23 in form of nozzle rollers.

In one embodiment, a two adjacent nozzle straighteners 23 particularly on one side of an optical fiber 6 being straightened by three nozzle straighteners 23 are arranged opposed to a third nozzle straightener 23 being between the two adjacent nozzle straighteners 23 particularly on the other side of the optical fiber 6.

In one embodiment, five nozzle straighteners 23 are arranged in the manner of the Olympic rings such that the optical fiber 6 can be fed between three adjacent nozzle straighteners 23 on one side and opposed two adjacent nozzle straighteners 23 on the other side particularly of the optical fiber 6.

In one embodiment, a nozzle straightener 23 has a cylindrical shape and/or a particularly circumferential groove.

In one embodiment, a nozzle straightener 23 has a flat surface and/or corrugated surface of the groove.

In one embodiment, a nozzle straightener 23 has a groove with v-shape or u-shape.

A corrugated surface facilitates processing of ferrous wires. A u-shaped groove facilitates processing of small diameter and/or ferrous wires.

Figure 8:
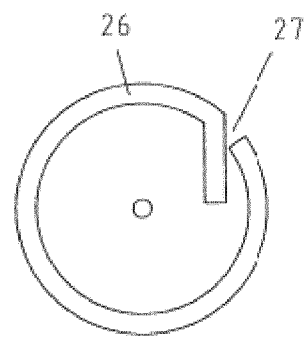

FIG. 7 shows a partly sectioned view of an exemplary optical cored wire 6 having an inner metal or semi tight plastic buffer layer 25 and an outer metal layer 26, i.e. the outer metal jacket. FIG. 8 shows a cross section view that schematically illustrate the seam 27 of the optical cored wire 6. In an embodiment, the optical cored wire 6 comprises a centered optical fiber 28 encompassed by an inner metal or semi tight plastic buffer layer 25 that is separated by a filler from the metal layer 26 in form of an outer metal jacket. In particular, the outer metal jacket or metal layer 26 being closed by the seam 27 better shown in the cross section view. Preferably, the inner metal and/or semi tight plastic buffer layer 25 can be composed of a bundle of straight wires being oriented in parallel to the optical fiber 28 and/or of a helically coiled wire turned about the optical fiber 28 or the bundle of straight wires. Particularly, the optical fiber 28 is immediately covered by a buffer sheathing 30 for further protection.

The invention claimed is:

1. A method for feeding an optical cored wire into a molten metal bath, the method comprising:
   decoiling an optical cored wire;
   feeding the decoiled optical cored wire in a feeding direction towards the molten metal bath and conducting a first straightening of the optical cored wire using a feeding and straightening device comprising a plurality of rollers; and
   conducting a second straightening of the optical cored wire to form a straightened optical cored wire, the second straightening conducted with a plurality of non-motor driven nozzle straighteners arranged between the feeding and straightening device and the molten metal bath.

2. The method of claim 1, further comprising releasing a purge gas around the straightened optical cored wire while feeding the straightened optical cored wire in the feeding direction.

3. The method of claim 1, wherein the straightened optical cored wire is released within a slag of the metal bath.

4. The method of claim 1, wherein the straightened optical cored wire is immersed into the metal bath under a right angle to a surface of the metal bath.

5. The method of claim 1, wherein the straightened optical cored wire is released at a distance closer to the metal bath than a vessel wall.

6. The method of claim 1, wherein an immersion nozzle between the feeding and straightening device and the metal bath comprises the separated further plurality of non-motor driven nozzle straighteners and releases the straightened optical cored wire above a surface of the metal bath.

7. An immersion nozzle to carry out the method of claim 1, for feeding the straightened optical cored wire into the metal bath in an immersion direction towards the metal bath, the immersion nozzle comprising a nozzle housing, the plurality of non-motor driven nozzle straighteners inside of the nozzle housing and a carrier pipe surrounded by the nozzle housing for guiding the optical cored wire, wherein a purge gas inlet allows supply of a purge gas into an annulus outside of the carrier pipe and inside of the nozzle housing, wherein a separation separates the plurality of non-motor driven nozzle straighteners from the annulus.

8. The immersion nozzle of claim 7, wherein an immersion end of the immersion nozzle in the feeding direction and/or the housing is composed to withstand conditions inside of a vessel containing the molten metal bath.

9. The immersion nozzle of claim 7, wherein the plurality of non-motor driven nozzle straighteners is arranged in the feeding direction prior to the carrier pipe.

10. The immersion nozzle of claim 7, wherein an overall length of the immersion nozzle is adjustable.

11. The immersion nozzle of claim 7, wherein at least two and/or at most ten nozzle straighteners form the plurality of non-motor driven nozzle straighteners.

12. The immersion nozzle of claim 7, wherein the plurality of non-motor driven nozzle straighteners are arranged such that each nozzle straightener is placed with a distance in the feeding direction to its immediate neighboring nozzle straightener and placed at another angle about an axis in feeding direction.

13. The immersion nozzle of claim 7, wherein a nozzle straightener of the plurality of non-motor driven nozzle straighteners has a groove.

14. The immersion nozzle of claim 7, wherein a connector is attached to a nozzle housing and encloses the plurality of nozzle straighteners for facilitating a changeable fixation to a guide tube.

15. An immersion nozzle to carry out the method of claim 1, for feeding the straightened optical cored wire into the metal bath in an immersion direction towards the metal bath, the immersion nozzle comprising the plurality of non-motor driven nozzle straighteners and a carrier pipe for guiding the optical cored wire.

16. An immersion system to carry out the method of claim 1, for feeding the straightened optical cored wire into the metal bath comprising the feeding and straightening device and an immersion nozzle, wherein the feeding and straightening device comprises a plurality of rollers for feeding the optical cored wire in the feeding direction towards the metal bath as well as a first straightening of the optical cored wire and the immersion nozzle comprises the plurality of non-motor driven nozzle straighteners.

17. The immersion nozzle of claim 8, wherein the immersion end of the immersion nozzle in the feeding direction and/or the housing is composed of steel and/or a ceramic material.

18. The immersion nozzle of claim 15, wherein an immersion end of the immersion nozzle in feeding direction is composed to withstand conditions inside of a vessel containing the molten metal bath.

19. The immersion nozzle of claim 13, wherein the groove has a v-shape and/or a corrugated surface.

20. The immersion nozzle of claim 13, wherein the groove has a u-shape and/or a corrugated surface.

* * * * *